United States Patent [19]

Kiesele et al.

[11] Patent Number: 5,719,325
[45] Date of Patent: Feb. 17, 1998

[54] GAS SENSOR

[75] Inventors: Herbert Kiesele; Michael Dietrich, both of Lübeck, Germany

[73] Assignee: Drägerwerk Aktiengesellschaft, Lübeck, Germany

[21] Appl. No.: 767,069

[22] Filed: Dec. 16, 1996

[30] Foreign Application Priority Data

Dec. 16, 1995 [DE] Germany ............... 195 47 150.4

[51] Int. Cl.⁶ ............... G01N 27/58; G01N 27/12; B05D 5/12
[52] U.S. Cl. ............... 73/31.06; 73/23.31; 73/23.2; 204/406; 204/424; 204/432; 422/90; 422/98
[58] Field of Search ............... 73/31.06; 204/431–432, 204/412, 406, 424; 422/98, 90

[56] References Cited

U.S. PATENT DOCUMENTS

| | | | |
|---|---|---|---|
| 4,338,281 | 7/1982 | Treitinger et al. | 422/98 |
| 4,345,985 | 8/1982 | Tohda et al. | 204/192 EC |
| 4,792,433 | 12/1988 | Katsura et al. | 422/98 |
| 4,824,548 | 4/1989 | Iino et al. | 204/406 |
| 5,215,643 | 1/1993 | Kusanagi et al. | 204/412 |
| 5,296,196 | 3/1994 | Takeshima | 422/98 |
| 5,429,727 | 7/1995 | Vogt et al. | 204/153.14 |
| 5,602,326 | 2/1997 | Takahashi et al. | 73/31.06 |
| 5,604,298 | 2/1997 | Dosoretz et al. | 73/23.2 |
| 5,608,154 | 3/1997 | Kato et al. | 73/23.31 |

FOREIGN PATENT DOCUMENTS 0310063 4/1989 European Pat. Off. .

Primary Examiner—Hezron E. Williams
Assistant Examiner—J. David Wiggins
Attorney, Agent, or Firm—Walter Ottesen

[57] ABSTRACT

A gas sensor has at least a measuring electrode and a counter electrode on an electrolyte layer. This gas sensor is improved with respect to the complete extent of the electrochemical reaction achieved of the gas molecules, which are to be detected, at the measuring electrode by the manner of determining an electrical charge developed or accumulated thereat. To solve this task, the invention provides that the measuring electrode (14) has component electrodes (14a, 14b) which enclose the electrolyte layer (11, 12) in the manner of a sandwich.

12 Claims, 2 Drawing Sheets

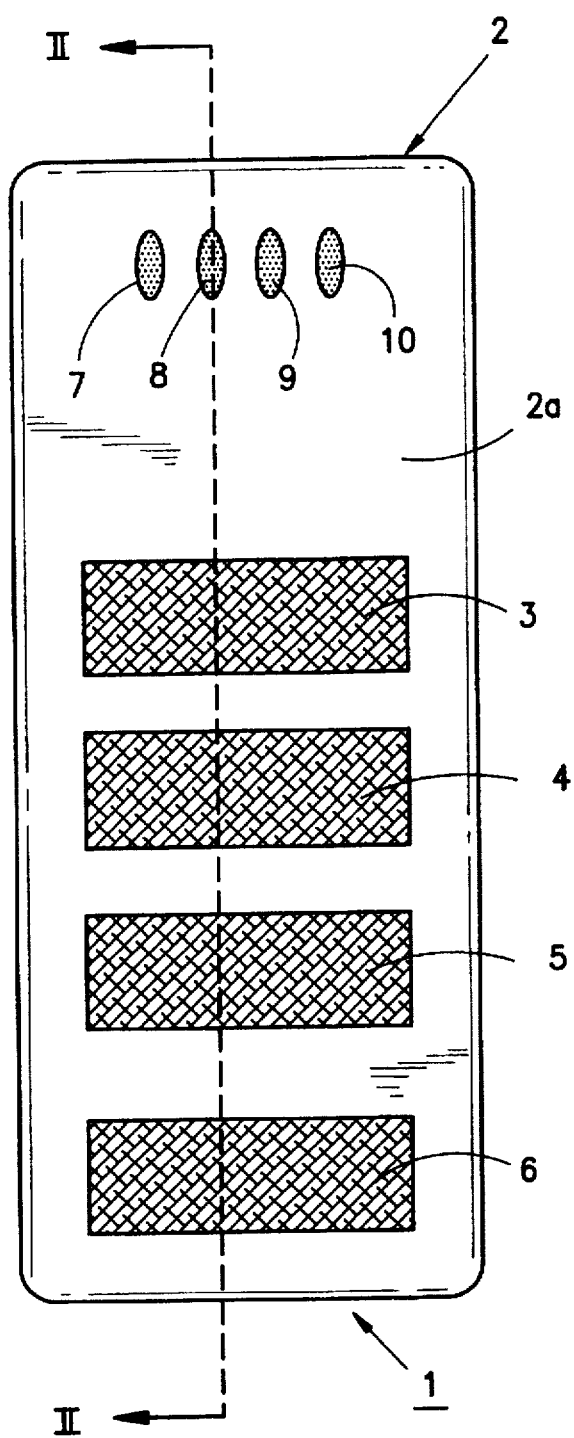
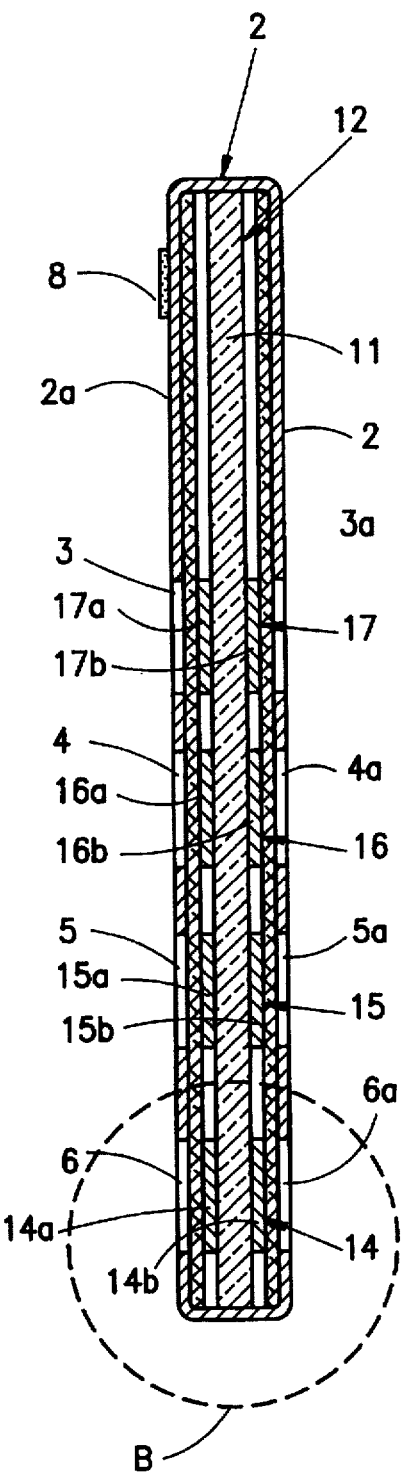
FIG. 1
FIG. 2

GAS SENSOR

BACKGROUND OF THE INVENTION

European published patent application 0.310.063 discloses a gas sensor having a measuring electrode, a counter electrode and an electrolyte disposed between the measuring electrode and the counter electrode. The gas molecules to be analyzed diffuse through a diffusion barrier and are, as they enter into the electrolyte layer, electrochemically converted at the three-phase boundary. The diffusion barrier lies upstream of the measuring electrode. The reference electrode is subjected directly to the ambient atmosphere as a reference gas. In the sensor configuration disclosed herein, it can occur that the gas molecules to be analyzed are not completely converted at the measuring electrode and diffuse into the electrolyte layer. Drift and memory effects can occur because of back diffusion to the measuring electrode and this can unfavorably affect the sensor signal.

SUMMARY OF THE INVENTION

It is an object of the invention to improve a gas sensor with respect to the electrochemical reaction of the gas molecules, which are to be detected, at the measuring electrode.

The gas sensor of the invention is for measuring a gas and includes: a measuring electrode permeable to the gas and having first and second gas permeable component measuring electrodes defining respective surfaces which can be subjected to the gas; counter electrode means; the component measuring electrodes being mutually adjacent so as to define a space therebetween; and, electrolyte means disposed in the space and interconnecting the counter electrode means and the measuring electrode.

The advantage of the invention is seen essentially in that the electrochemical conversion of the gas molecules to be detected is improved by configuring the electrode to provide a multisided covering of the electrolyte. The measuring electrode then exhibits individual measuring fields. The electrochemical conversion is improved because the gas molecules, which are not oxidized at one measuring field, react electrochemically at the adjacent lying measuring field and therefore cannot penetrate areally into the electrolyte layer. An especially good electrochemical conversion of the gas molecules is obtained when the measuring fields are arranged to be at least partially overlapping or are arranged at an angle with respect to each other. In the simplest case, the measuring fields lie matually adjacent and are parallelly spaced. However, concentric arrangements are also possible such as on a porous tubular body filled with an electrolyte.

It is especially advantageous to configure the measuring electrode as a double measuring electrode so that the measuring electrode fields cover the electrolyte in a sandwich-like manner. The double measuring electrode then has two sides both of which can be subjected to the gas.

In an advantageous manner, a second double measuring electrode is provided to detect an additional gas component. This second double measuring electrode covers the electrolyte layer. A reference electrode also provided which is configured as a double reference electrode.

Advantageously, the counter electrode is configured as a double counter electrode which encloses the electrolyte layer in the manner of a sandwich.

The measuring double electrodes, the double counter electrode and a double reference electrode are all advantageously applied to a gas-permeable membrane which encloses the electrolyte layer in the manner of a foil wrapper covering.

The sandwich-like configuration provides that the first component electrodes are on the upper side of the electrolyte layer and the second component electrodes are on the lower side of the electrolyte layer. The respective first component electrodes of the measuring electrode, the reference electrode and the counter electrode are arranged on a first membrane surface and the respective second component electrodes of the measuring electrodes, the reference electrode and the counter electrode are applied to a second membrane surface. The membrane surfaces each cover the upper and lower sides of the electrolyte layer so that the electrodes are in contact with the electrolyte. The two membrane surfaces can be connected to each other by means of a fixed frame which extends on the outer sides of the electrolyte layer. The frame then imparts the necessary stability to the gas sensor. The membrane surfaces are advantageously produced from PTFE (polytetrafluoroethylene).

In an advantageous manner, the electrolyte layer is configured as a nonwoven fabric impregnated with liquid electrolyte or is configured as a gel electrolyte layer. The electrolyte carrier can also comprise a porous glass, ceramic or plastic. Furthermore, a polymer electrolyte can be used as an electrolyte layer.

In an advantageous manner, the measuring electrode comprises a porous conductive body impregnated with electrolyte. This body is subjected directly to the gas sample to be investigated. The electrolyte layer fills the pores of the body and the body is subjected on all sides to the gas to be measured. The conductive body can, for example, be sintered metal, metal foam or "porous carbon".

BRIEF DESCRIPTION OF THE DRAWINGS

The invention will now be described with reference to the drawings wherein:

FIG. 1 is a plan view of a gas sensor according to a first embodiment of the invention;

FIG. 2 is a side elevation view, in section, of the gas sensor in longitudinal section taken along line II—II of FIG. 1;

DESCRIPTION OF THE PREFERRED EMBODIMENTS OF THE INVENTION

Figure 3:
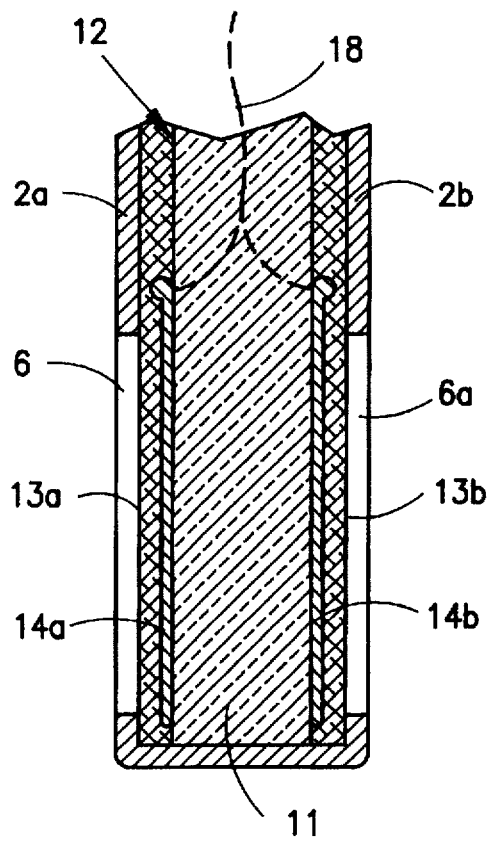
FIG. 3 is an expanded view of detail B portion of FIG. 2.

FIG. 1 shows a plan view of a sensor upper part 2a of a first embodiment of a gas sensor 1. The sensor upper part 2a has windows 3, 4, 5 and 6 through which gas molecules (not shown) can diffuse to electrodes (not shown in FIG. 1) located within the gas sensor. Contact points 7, 8, 9 and 10 are provided on the sensor upper part 2a and these contact points are connected to respective electrodes (not shown in FIG. 1).

FIG. 2 shows the first gas sensor 1 in longitudinal section along section line II—II of FIG. 1. The same components are here identified by the same reference numerals as in FIG. 1. The rear side of the gas sensor 1 is closed with a sensor lower part 2b which likewise has windows identified by reference numerals 3a, 4a, 5a and 6a. These windows lie aligned with parallel to and opposite to the windows 3, 4, 5 and 6. The sensor upper part 2a and the sensor lower part 2b conjointly define a sensor housing 2. A thin nonwoven fabric 12 is impregnated with an electrolyte 11 and is located centrally within the sensor housing 2. The nonwoven fabric 12 is arranged sandwich-like between a first gas-permeable PTFE membrane 13a and a second gas-permeable PTFE membrane 13b.

The inner sides of membranes 13a, 13b face toward the electrolyte 11. A first double measuring electrode 14 having component electrodes (14a, 14b) is applied to the inner sides of the membranes (13a, 13b) at the elevation of the windows 6, 6a as best shown in FIG. 3. A second double measuring electrode 15 having component electrodes (15a, 15b) is provided at the elevation of windows 5, 5a and a double reference electrode 16 having component electrodes (16a, 16b) is provided at the elevation of windows 4, 4a and a double counter electrode 17 having component electrodes (17a, 17b) is provided at the elevation of windows 3, 3a. The electrodes 14, 15, 16 and 17 are each arranged sandwich-like with respect to the nonwoven fabric 12 impregnated with electrolyte 11. Opposite-lying electrode components of each electrode are connected to each other as shown in FIG. 3 for the first double measuring electrode 14. The measuring electrodes 14, 15 are gas permeable.

Referring to FIG. 3, the double measuring electrode 14 defines two measuring fields, with its first component electrode 14a and its second component electrode 14b. These component electrodes are connected via a common contact lead 18 to the contact point 7 of FIG. 1. In the same manner, the second double measuring electrode 15 is connected to the contact point 8 and the double reference electrode 16 is connected to contact point 9 of FIG. 1. The double counter electrode 17 is connected to contact point 10 of FIG. 1. The electrodes 14, 15, 16 and 17 are connected to a potentiostat as known per se.

The operation of the gas sensor 1 of the invention takes place in that the potentiostat is continuously connected to the electrodes 14, 15, 16 and 17; and the gas components, which penetrate to the measuring electrodes 14, 15, are directly converted or, during a so-called "collecting phase", at least the measuring electrodes 14, 15 are disconnected from the potentiostat and the components to be detected collect in the intermediate space between the component electrodes of measuring electrodes 14, 15. At the start of the so-called "measuring phase", the connection between the measuring electrodes 14, 15 and the potentiostat is again established and a constant potential is applied to the measuring electrodes 14, 15. The gas components collected in the electrolyte 11 are then oxidized or reduced at each of the components of the measuring electrodes 14, 15 in dependence upon the pregiven potential. The resulting electrical charge, which is measured during a fixed time after switching on the measuring electrode, is used as a measure for the gas concentration.

The operation of the first gas sensor 1 will now be described.

The gas sensor 1 permits two gas components to be detected in the gas sample. A first component is converted at the first double measuring electrode 14 and the second component is converted at the second double measuring electrode 15. Because of the entry of the gas at both sides of the sensor via the windows 6, 6a, 5, 5a, the area of the measuring electrode surface is doubled compared to conventional configurations and, because of the sandwich-like mutually opposite component electrodes of the measuring electrodes 14, 15, the gas components, which, for example, diffuse in via the component electrode 14a but have not been converted at the component electrode 14a, are oxidized at the opposite-lying component electrode 14b. The same applies to gas components which diffuse in via the component electrode 14b to the component electrode 14a. The thickness of the electrolyte layer, that is, the thickness of the nonwoven fabric 12 is selected in accordance with the particular application. For coulometric measurements with discontinuous operation, a nonwoven fabric thickness of less than 0.5 mm is advantageous. The nonwoven fabric can have a thickness of greater than 1 mm for amperometric measurements as characterized by continuous operation.

Figure 4:
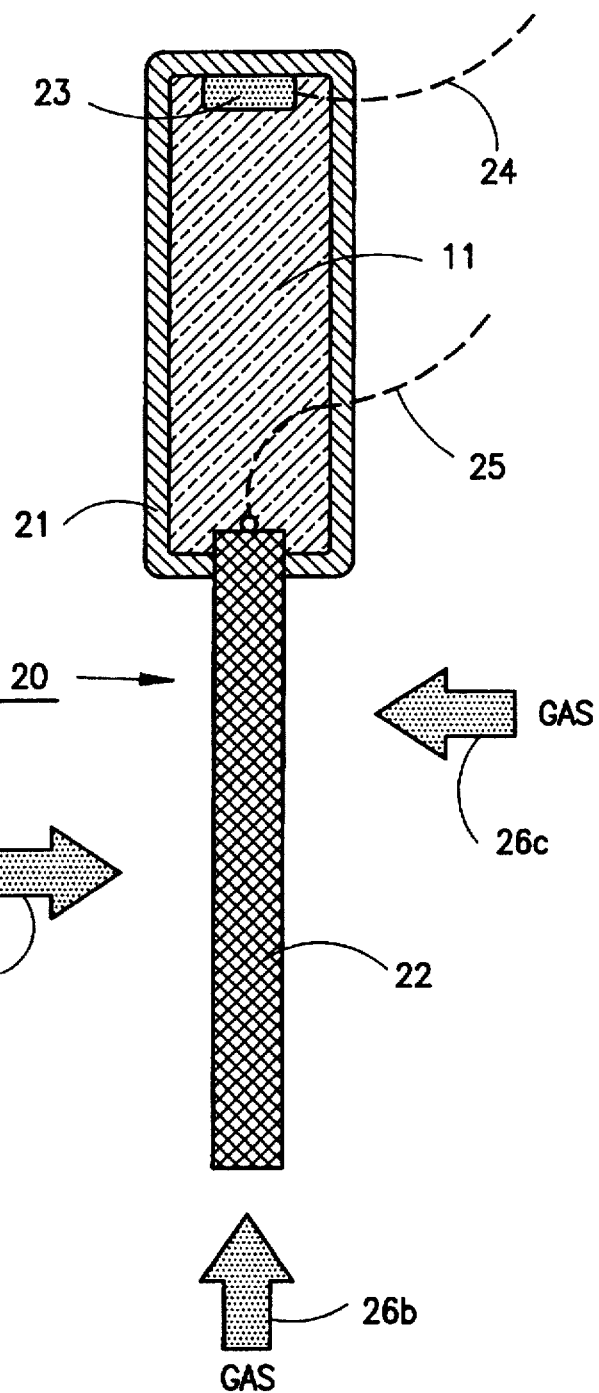
FIG. 4 is a section view of a second embodiment of the gas sensor of the invention wherein the gas sensor has a sinter metal body as a measuring electrode.

FIG. 4 schematically shows the configuration of a second gas sensor 20 embodiment with a different type of measuring electrode. This gas sensor has a measuring electrode comprising a sintered metal body type of measuring electrode 22 and a counter electrode 23 which are connected to each other via an electrolyte 11. The measuring electrode 22 is secured in a measuring cell housing 21. The measuring electrode 22 comprises a porous sinter metal body which is impregnated with the electrolyte 11. The electrodes 22, 23 are connected via respective contact leads 24, 25 to an evaluation circuit not shown in FIG. 4. The gas molecules to be detected diffuse in the direction of the arrows (26a, 26b, 26c) into the sinter metal body of measuring electrode 22 and react there with the electrolyte 11. Because of the porosity of the sinter metal body measuring electrode 22 and the large surface area associated therewith, the gas molecules diffusing in via the sinter metal body 22 can be completely oxidized.

It is understood that the foregoing description is that of the preferred embodiments of the invention and that various changes and modifications may be made thereto without departing from the spirit and scope of the invention as defined in the appended claims.

What is claimed is:

1. A gas sensor for measuring a gas, the gas sensor comprising:

a measuring electrode permeable to said gas to be measured;

said measuring electrode having structure defining first and second individual surfaces which can be subjected to the gas;

said individual surfaces being mutually adjacent and defining a space therebetween;

counter electrode means;

electrolyte means interconnecting said counter electrode and said measuring electrode and at least a portion of said electrolyte means being disposed in said space;

said structure being a conductive porous body defining said individual surfaces; and, said electrolyte means including an electrolyte impregnated in said porous body.

2. The gas sensor of claim 1, said body being a sinter metal body.

3. The gas sensor of claim 1, said body being made of a material selected from the group consisting of metal foam and porous carbon.

4. A gas sensor for measuring a gas, the gas sensor comprising:

a measuring electrode permeable to said gas and having first and second gas permeable component measuring electrodes defining respective surfaces which can be subjected to the gas;

counter electrode means;

said component measuring electrodes being mutually adjacent so as to define a space therebetween;

electrolyte means disposed in said space and interconnecting said counter electrode means and said measuring electrode;

said component measuring electrodes and said electrolyte means conjointly defining a sandwich-like structure;

said measuring electrodes being a first measuring electrode and said space being a first space;

a second measuring electrode having first and second ancillary measuring electrodes conjointly defining a second space therebetween; and, said electrolyte means extending into said second space whereby said ancillary measuring electrodes and said electrolyte means also define a sandwich-like structure.

5. The gas sensor of claim 4, said counter electrode means including a counter electrode having first and second component counter electrodes conjointly defining a third space therebetween; and, said electrolyte means also extending into said third space whereby said component counter electrodes and said electrolyte means also define a sandwich-like structure.

6. The gas sensor of claim 5, further comprising a reference electrode including first and second component reference electrodes conjointly defining a fourth space therebetween; and, said electrolyte means also extending into said fourth space whereby said component reference electrodes and said electrolyte means also conjointly define a sandwich-like structure.

7. The gas sensor of claim 6, further comprising a membrane permeable to said gas and foil-like enclosing said electrolyte means; and, said component measuring electrodes, said ancillary measuring electrodes, said component counter electrodes and said component reference electrodes all being arranged on said membrane.

8. The gas sensor of claim 7, said electrolyte means including a nonwoven fabric and a liquid electrolyte impregnated in said nonwoven fabric.

9. The gas sensor of claim 7, said electrolyte means being configured as a gel electrolyte layer.

10. The gas sensor of claim 4, said component measuring electrodes being mutually parallel.

11. A gas sensor for measuring a gas, the gas sensor comprising:

a measuring electrode permeable to said gas and having first and second gas permeable component measuring electrodes defining respective surfaces which can be subjected to the gas;

said component measuring electrodes being mutually adjacent so as to define a space therebetween;

counter electrode means;

said counter electrode means having first and second component counter electrodes conjointly defining a space therebetween;

electrolyte means disposed in said spaces and interconnecting said component measuring electrodes and said component counter electrodes; and, said component measuring electrodes, said component counter electrodes and said electrolyte means conjointly defining a sandwich-like structure.

12. The gas sensor of claim 11, further comprising a reference electrode including first and second component reference electrodes conjointly defining a space therebetween; and, said electrolyte means also extending into said space between said reference electrodes.

* * * * *